(12) United States Patent
Taguchi et al.

(10) Patent No.: US 9,017,739 B2
(45) Date of Patent: Apr. 28, 2015

(54) METHOD FOR SUPPRESSING AND RELIEVING ITCHING AND INFLAMMATION

(71) Applicants: Kazue Taguchi, Tokyo (JP); Shigeru Taguchi, Tokyo (JP); Yutaka Sashida, Tokyo (JP)

(72) Inventors: Kazue Taguchi, Tokyo (JP); Shigeru Taguchi, Tokyo (JP); Yutaka Sashida, Tokyo (JP)

(73) Assignees: Kands R&D Corporation, Tokyo (JP); Erina Co., Inc., Tokyo (JP)

( * ) Notice: Subject to any disclaimer, the term of this patent is extended or adjusted under 35 U.S.C. 154(b) by 0 days.

(21) Appl. No.: 14/517,818

(22) Filed: Oct. 18, 2014

(65) Prior Publication Data

US 2015/0037440 A1   Feb. 5, 2015

Related U.S. Application Data

(62) Division of application No. 13/371,085, filed on Feb. 10, 2012, now Pat. No. 8,889,198, which is a division of application No. 12/224,193, filed as application No. PCT/JP2007/052978 on Feb. 19, 2007, now abandoned.

(30) Foreign Application Priority Data

Feb. 22, 2006 (JP) ................................ 2006-044801

(51) Int. Cl.
  *A01N 65/00* (2009.01)
  *A61K 36/752* (2006.01)
  *A23L 1/30* (2006.01)
  *A23L 2/52* (2006.01)

(52) U.S. Cl.
  CPC .............. *A61K 36/752* (2013.01); *A23L 1/3002* (2013.01); *A23L 2/52* (2013.01); *A23V 2002/00* (2013.01)

(58) Field of Classification Search
  None
  See application file for complete search history.

(56) References Cited

U.S. PATENT DOCUMENTS

2004/0053860 A1 *  3/2004  Buchholz et al. ............... 514/27

* cited by examiner

*Primary Examiner* — Michael Meller
(74) *Attorney, Agent, or Firm* — Marshall & Melhorn, LLC

(57) ABSTRACT

The present invention provides a method for suppressing and relieving itching and inflammation, by administering to a host in need of such treatment an effective amount of the pharmaceutical composition containing highly lipophilic polyalkoxyflavonoid. The pharmaceutical composition and functional food of the present invention for suppressing and relieving itching and inflammation contain highly lipophilic polyalkoxyflavonoid extracted from squeezed juice of a whole portion of a citrus fruit (inclusive of pericarp thereof). Furthermore, the functional food of the present invention contains it.

5 Claims, 4 Drawing Sheets

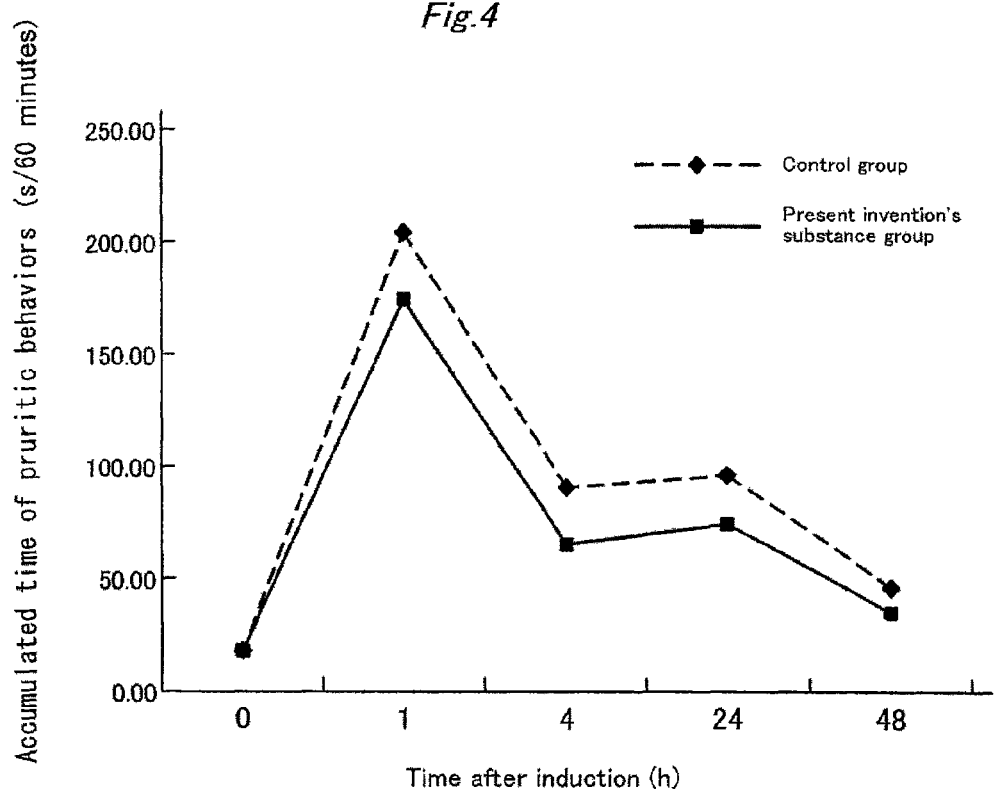

METHOD FOR SUPPRESSING AND RELIEVING ITCHING AND INFLAMMATION

CROSS-REFERENCE TO RELATED APPLICATIONS

This application is a divisional of and, pursuant to 35 U.S.C. §120, claims the benefit of U.S. patent application Ser. No. 13/371,085, filed Feb. 10, 2012, which is pending as of the filing date of this application. U.S. patent application Ser. No. 13/371,085 is a divisional of and claims the benefit of U.S. patent application Ser. No. 12/224,193, filed on Jan. 21, 2009. U.S. application Ser. No. 12/224,193, pursuant to 35 U.S.C. §371, is the U.S. national phase of international patent application PCT/JP2007/052978, filed Feb. 19, 2007, and claims priority to application number JP-2006-044801, filed Feb. 22, 2006. application Ser. Nos. 13/371,085, 12/224,193, PCT/JP2007/052978, and JP-2006-044801 are hereby incorporated by reference in their entireties to the extent permitted by law.

FIELD OF THE INVENTION

The present invention relates to pharmaceutical compositions for suppressing and relieving itching and inflammation, as well as functional food that can be used in combination with ethical medicaments to enhance the therapeutic effect thereof without causing side effects.

BACKGROUND OF THE INVENTION

Most of the cutaneous diseases are generally accompanied by itching. Suppression and relief of such itching are one of the most important tasks in the clinical practice of today, because many dermatologists mention that the aggravation of, for example, atopic dermatitis can be prevented only if the itching can be suppressed.

Such itching includes general pruritus which is defined as that is suppressible by commercially available antipruritic drugs such as anti-histamine drugs, and inveterate pruritus, which is defined as that cannot be suppressed by anti-histamine drugs nor by steroid drugs, such as dermal pruritus in hemodialysed patients, senile pruritus, and atopic dermatitis. The commercially available general antipruritic drugs based on anti-histamine agents are not only ineffective against inveterate pruritus, but also have the drawback of causing side effects such as drowsiness (central inhibition).

Although tacrolimus hydrate ointment, an immune suppressor, has recently been reported to be effective in treating atopic dermatitis (see JP2002-338537), this agent is not well-understood regarding its safeness and it is concerned that the agent may induce skin cancer and induce renal impairment when a significant amount is absorbed from an eroded site of the skin into the body.

SUMMARY OF THE INVENTION

The present invention is made to solve above problems of the prior art and its main object is to provide a pharmaceutical composition and functional food capable of suppressing and relieving all types of itching including general pruritus and inveterate pruritus safely, as well as inflammation.

To achieve the object, the present invention provides a pharmaceutical composition containing highly lipophilic polyalkoxyflavonoid extracted from squeezed juice of a whole portion of a citrus fruit, including pericarp thereof. Preferably, the citrus fruit may be selected from a group consisting of *Citrus tachibana, Citrus deliciosa, Citrus kinokuni, Citrus erythrosa, Citrus tangerina, Citrus sunki, Citrus depressa, Citrus tardiva,* and *Citrus retuculata* which belong to Acrumen group, and *Citrus hanayu* and *Citrus calamondin*, a dwarf type of citrus cultivated in Southeast Asia, which belong to Osmocitrus group. In addition, these pharmaceutical compositions are preferably contained in functional food.

The present invention can safely suppress and relieve not only general pruritus but also inveterate pruritus as well as inflammation without causing side effects such as drowsiness, and thus is highly beneficial in preventing, improving, or treating diseases involving cutaneous symptoms.

BRIEF DESCRIPTION OF THE DRAWINGS

FIG. 4 is a graph comparing the accumulated time of pruritic behaviors of control group and that of group administered (internally) with the substance of the present invention.

DETAILED DESCRIPTION OF THE PREFERRED EMBODIMENT(S)

Figure 1:
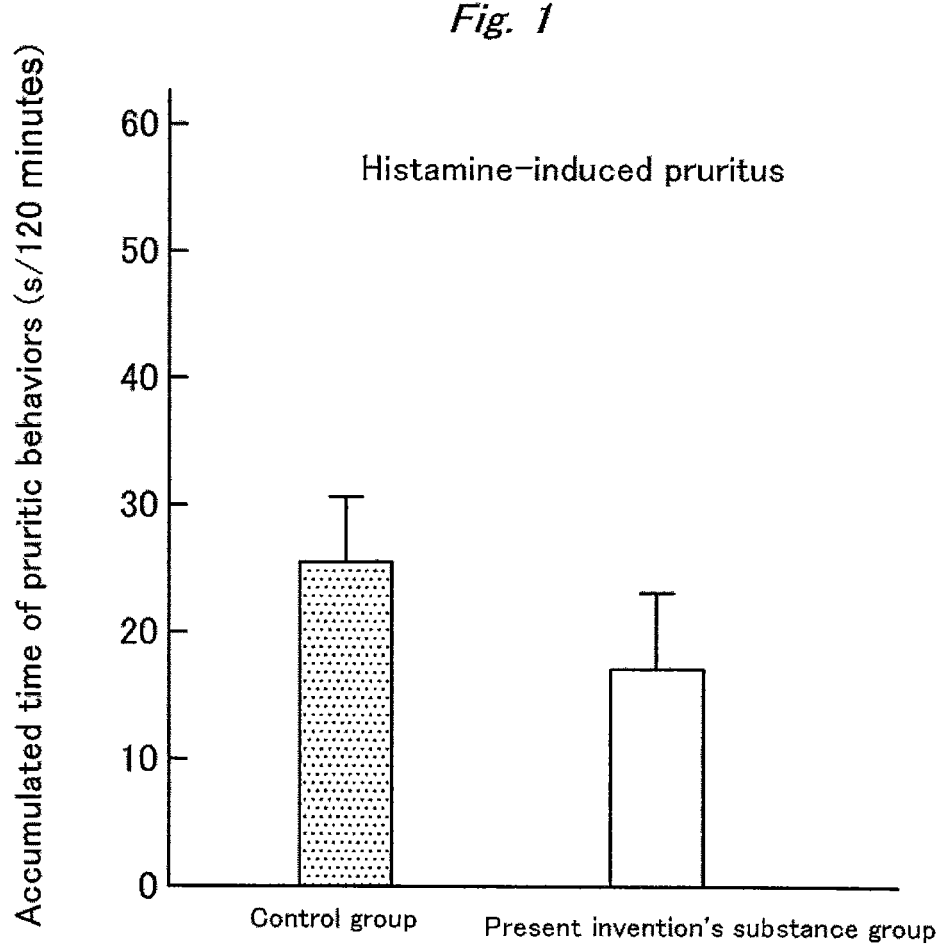
FIG. 1 is a graph comparing the cumulative time of pruritic behaviors in control group and that in group administered (externally) with the substance of the present invention, each having histamine-induced pruritus.

Now, the present invention is described below in more detail with reference to the attached drawings.

The substance which shows antipruritic and anti-inflammatory effects according to the present invention is the highly lipophilic polyalkoxyflavonoid contained in squeezed juice of a whole portion of a citrus fruit (inclusive of the pericarp thereof). This substance is contained in citrus fruits (inclusive of the pericarp thereof) selected from a group consisting of *Citrus tachibana, Citrus deliciosa, Citrus kinokuni, Citrus erythrosa, Citrus tangerina, Citrus sunki, Citrus depressa, Citrus tardiva,* and *Citrus retuculata* which belong to Acrumen group, and *Citrus hanayu* and *Citrus calamondin*, a dwarf type of citrus cultivated in Southeast Asia, which belong to Osmocitrus group, and can be readily extracted from the squeezed juice of the whole portion of these fruits.

Since the highly lipophilic polyalkoxyflavonoid of the present invention is included in the pericarp of citrus in a large amount, it is extracted from a solution, which is obtained by mixing the juice from a whole portion of a citrus fruit thereof by press-squeezing or centrifuging, and the pulverized residue of the fruit, by using the known purification techniques. See "Polymethoxylated Flavnoids from the Peels of Citrus depressa" (Yoshihiro Mimaki et al., Natural Medicines, 2000, 54 (6): 351), as needed.

The fractionated highly lipophilic polyalkoxyflavonoid is further eluted with lipophilic solvent to obtain eluate containing the highly lipophilic polyalkoxyflavonoid (tangeritin, nobiletine). Powdered preparation can be obtained by spray-drying or freeze-drying of the concentrated eluate.

[Verification of the Antipruritic Effect by External Use]

Next, the verification results of the antipruritic effect of the substance of the present invention (highly lipophilic polyalkoxyflavonoid) extracted as above are described.

First, general pruritus and inveterate pruritus appearance model animals were induced by using guinea pigs. Specifically, 8 weeks old male Hartley guinea pigs were shaved on the right ventral region with an electric shaver and a shaver 1 day before the experiment. Those to be used as a general pruritus model were intracutaneously administered with histamine hydrochloride (0.3 mg/ml), and those to be used as an inveterate pruritus model were intracutaneously administered with swine spleen kallikrein (25 U/0.05 ml) to induce pruritus. This provided animal models of pruritus that allow evaluation of antipruritic effect on both of general pruritus, which can be suppressed by the conventional antipruritic drugs, and the inveterate pruritus, which cannot be suppressed by the conventional antipruritic drugs (see "Evaluation of antipruritic effect of apple polyphenols using a new animal model of pruritus", The Journal of Tokyo Medical University, 2002, Vol. 60, No. 2: 123-129).

These animal models were respectively divided into two groups so as that each group contain a desirable number of animals, for example, 12 animals. For the first group (control group), 100 µL of 10% glycerin solution was uniformly applied to their pruritic site (external use). For the second group (test substance group), 100 µl of 10% glycerin solution containing 1% of the substance of the present invention was similarly applied to their corresponding site. Pruritic behaviors (such as scratching the pruritic site with teeth or hind legs) of each animal group were observed and recorded for a predetermined period of time (2 hours) using an overhead video camera with time display, and cumulative time of pruritic behaviors of each group was measured (seconds/120 minutes). The presence or absence of the antipruritic effect in each group was determined using significant difference test based on the cumulative time of the pruritic behaviors. The results were expressed as means±standard deviations, and Dunnett's t-test was used as the significant difference test.

As shown in FIG. 1, for the groups having histamine-induced pruritus (the general pruritus), the cumulative time of the pruritic behaviors was 25.50±5.11 (s/120 minutes) in the control group and 17.08±5.26 (s/120 minutes) in the group administered with the substance of the present invention, showing a significant suppressive effect of the substance of the present invention on the pruritus.

Figure 2:
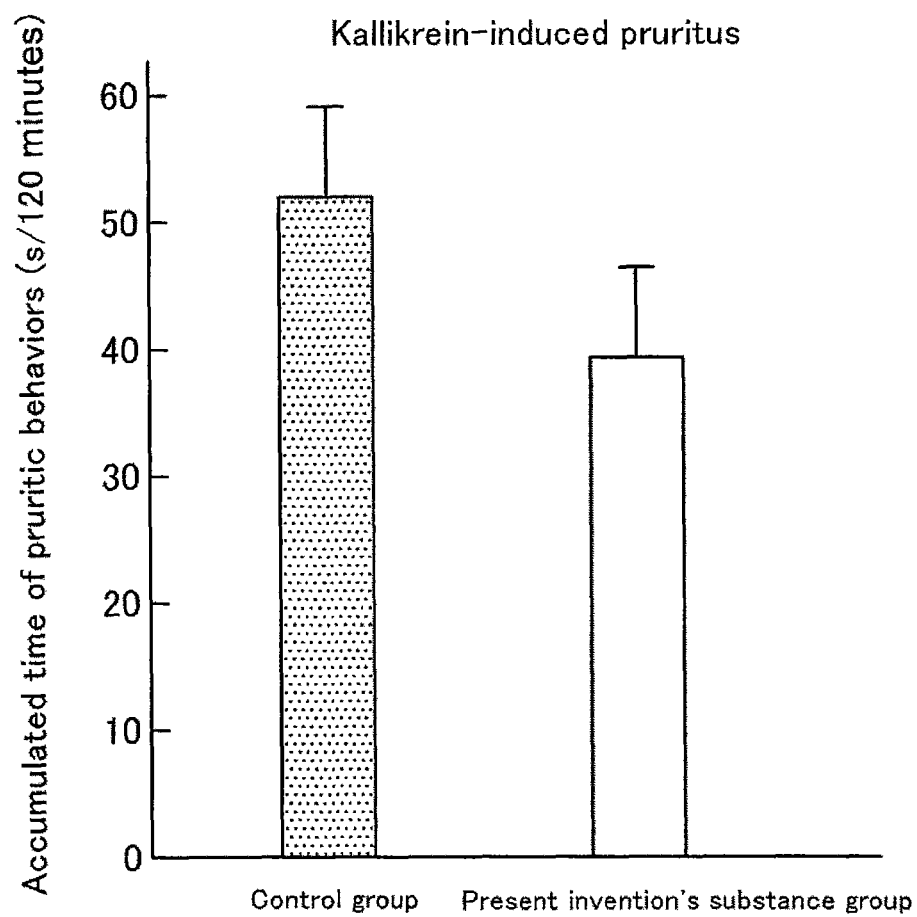
FIG. 2 is a graph comparing the cumulative time of pruritic behaviors in control group and that in group administered (externally) with the substance of the present invention, each having kallikrein-induced pruritus.

In addition, as shown in FIG. 2, for the groups having kallikrein-induced pruritus (inveterate pruritus), the cumulative time of the pruritic behaviors was 52.00±7.08 (s/120 minutes) in the control group and 39.33±6.39 (s/120 minutes) in the group administered with the substance of the present invention, showing also a significant antipruritic effect of the substance of the present invention.

Thus, these results show that the substance of the present invention with a sufficient concentration of 1% or more provides an antipruritic effect not only on histamine-induced pruritus but also on kallikrein-induced pruritus, which cannot be suppressed by the anti-histamine drugs at all, with the same effectiveness.

[Verification of the Anti-Inflammatory Effect by Internal Use]

Next, the anti-inflammatory effect of the substance of the present invention by internal use was verified.

5 weeks old female ICR mice were divided into two groups each consisting of 12 mice. The first group (the control group) and the second group received 0.3% carboxycellulose (CMC) suspension and 100 mg/kg of the substance of the present invention in 0.3% CMC suspension, respectively, via gavage administration with gastric sound for one week. The animals were allowed to take water and food voluntarily. 8 days after the administration, the mice were passively sensitized by intravenous administration into caudal vein of 0.5 mL monoclonal anti-DNP IgE antibody as antigen to elicit cutaneous reaction. One hour after the elicitation, 0.15% DNFB (dinitrofluorobenzene; Nakarai Kagaku. Ind. Co., Japan) solution prepared with acetone-olive oil (4:1) was applied to the auricle of the animals to induce dermatitis. At 1, 4, 24, and 48 hours after the induction of dermatitis, auricular thickening which indicates the degree of dermatitis was measured for each group using Dial Thickness Gauge (Mitsutoyo Corporation, Kanagawa, Japan).

Figure 3:
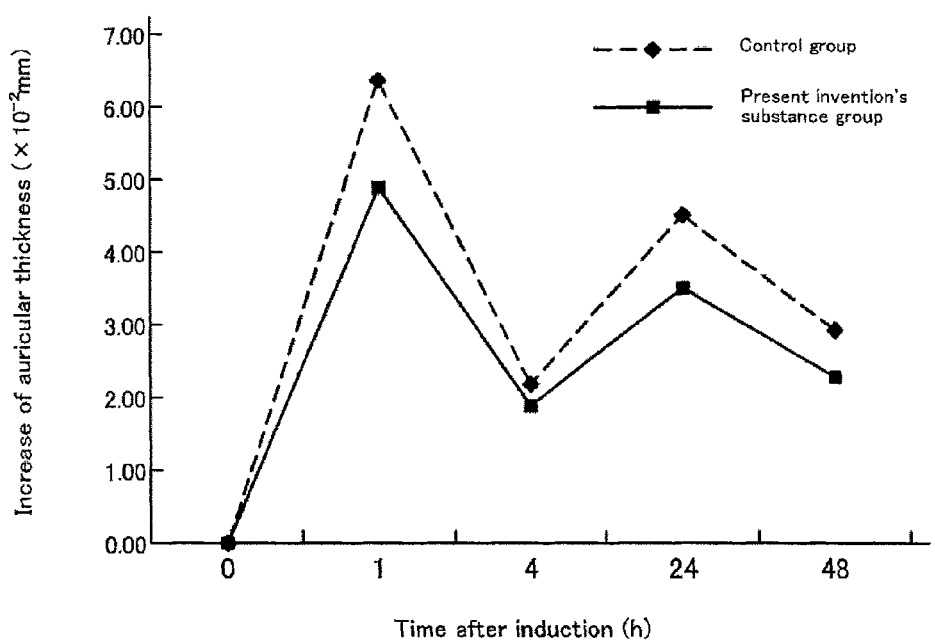
FIG. 3 is a graph comparing the auricular thickening of control group and that of group administered (internally) with the substance of the present invention.

As shown in FIG. 3, in the control group, the biphasic dermatitis was 6.33±0.41×10-2 mm and 4.49±0.45×10-2 mm at 1 and 24 hours after the induction, respectively, while in the group administered with the substance of the present invention, the biphasic dermatitis was 4.87±0.50×10-2 mm and 3.47±0.55×10-2 mm at 1 and 24 hours after the induction, respectively, showing a significant anti-inflammatory effect of the substance of the present invention.

[Verification of the Antipruritic Effect by the Internal Use]

In parallel with auricular thickening measurement, the pruritic behaviors of the animals were also observed for a predetermined period of time (1 hour) using the above-mentioned video camera with time display. As shown in the FIG. 4, in the control group, the cumulative time of the pruritic behaviors was 202.17±21.31 (s/60 minutes) and 95.92±24.54 (s/60 minutes) at 1 and 24 hours after the induction, respectively, while in the group administered with the test substance, the cumulative time of the pruritic behaviors was 173.50±22.39 (s/60 minutes) and 72.83±12.83 (s/60 minutes) at 1 and 24 hours after the induction, respectively, showing a significant effect of the substance of the present invention even when being used internally.

In the cutaneous reaction of the mice passively sensitized with IgE antibody, the biphasic inflammation consisting of immediate hypersensitivity of type I allergy and delayed allergy (type IV allergy), where eosinophil infiltration occurs, was observed. The immediate hypersensitivity corresponds to rhinitis, hay fever, and asthma etc., while late allergy corresponds to atopic dermatitis. Namely, compared to the control mice group, which didn't receive the substance of the present invention, in the mice group previously administered with the substance of the present invention, the inflammation induced by the passive sensitization with IgE antibody and application of DNFB, as well as the accompanying itchiness were significantly suppressed over 24 hours. This shows that the substance of the present invention suppressed and relieved type I allergy, which reached its peak one hour after its induction, and type IV allergy, which reached its peak 24 hours after its induction.

Therefore, the present invention has been found to be effective in suppressing and relieving the symptoms of type I allergic diseases related with immunoglobulin E such as rhinitis, hay fever, and asthma etc., as well as the symptoms of type IV allergic diseases such as atopic dermatitis, which are caused by various antigens such as house dust, pollens, spores, which are inhaled, dietary and alimentary allergens. In addition, the pruritus was biphasic consisting of immediate hypersensitivity (after one hour) corresponding to the histamine-induced pruritus (general pruritus) and delayed type one (after 24 hours) corresponding to kallikrein-induced pruritus (inveterate pruritus).

The above evaluation method can be easily used to screen an effective substance which can suppress or relieve the symptoms of type I allergic diseases associated with IgE antibodies at the same time. For the detail of this method, see Pharmacometrics, Vol. 69, No. 1/2, 47-51 published on Oct. 1, 2005.

On using the highly lipophilic polyalkoxyflavonoid of the present invention as a medicament, an effective amount of the highly lipophilic polyalkoxyflavonoid for inhibiting and treating pruritus may be preferably formulated with pharmaceutically acceptable carriers or diluents. Other additives such as binding agents, absorption promoters, lubricants, emulsifiers, surfactants, antioxidants, preservatives, colorants, flavors, sweeteners may be added.

In such formulation, the ratio of highly lipophilic polyalkoxyflavonoid, which is the active ingredient, to carriers is at the range of 0.05-30.0 weight %, preferably at the range of 0.1-5.0 weight %.

As the dosage form of the medicament, there can be mentioned such as cataplasm, spray, liquid, suspension, ointment, gel, paste, cream, granules, fine granules, tablet, pill, and capsule. As their administration routes, there can be mentioned various administration routes such as patches, skin application, per os, intravenous, intramuscular, subcutaneous, and administration into a joint cavity, and an external preparation is preferable. In case of using the substance of the present invention for skin as the external preparation for skin, the typical components contained in the general products used for skin external preparations can be combined with the substance of the present invention, if needed. In addition, the dosage and the dose frequency of the active ingredient can be varied according to the disease condition, age, and sex of a given patient, as well as the administration route.

The pharmaceutical composition containing the highly lipophilic polyalkoxyflavonoid of the present invention can be added to various food and beverage products such as snack and soft drink as a functional food for suppressing and relieving itching and inflammation. Functional food is defined as a food which was made to exert sufficient physiological functions (third function) such as biological regulation function, comprising natural products or processed ones thereof including one or more nutrient factors (see "Kenkou/EiyouShokuhin Advisory Staff Textbook, 92-93" published by Daichi Shuppan on Jul. 30, 2003).

In accordance with the provisions of the patent statutes, the present invention has been described in what is considered to represent its preferred embodiments. However, it should be noted that the invention can be practiced otherwise than as specifically illustrated and described without departing from its spirit or scope.

What is claimed is:

1. A method for relieving inveterate pruritus that cannot be suppressed by anti-histamine drugs nor by steroid drugs in a human, comprising administering to said human a therapeutically effective amount of an extract of *Citrus depressa* to relieve inveterate pruritus in said human, wherein said extract is administered in a form selected from the group consisting of granules, fine granules, tablet, pill, and capsule.

2. The method for relieving inveterate pruritus according to claim 1, wherein the extract of *Citrus depressa* to relieve inveterate pruritus in said human is administered in said human per os.

3. The method for relieving inveterate pruritus according to claim 1, wherein the extract of *Citrus depressa* to relieve inveterate pruritus in said human is added to a food.

4. The method for relieving inveterate pruritus according to claim 1, wherein the extract of *Citrus depressa* to relieve inveterate pruritus in said human is added to a beverage.

5. The method for relieving inveterate pruritus according to claim 1, wherein the extract of *Citrus depressa* to relieve inveterate pruritus in said human is extracted from squeezed juice of a whole portion of a citrus fruit, including pericarp thereof.

* * * * *